United States Patent [19]

Passarotti et al.

[11] Patent Number: 5,013,554

[45] Date of Patent: May 7, 1991

[54] ORAL PHARMACEUTICAL COMPOSITIONS CONTAINING DEXTROPHAN SALTS

[75] Inventors: Carlos Passarotti; Antonio Fossati; Mauro Valenti; Gianluigi Bandi, all of Milan, Italy

[73] Assignee: Prodotti Formenti s.r.l., Milan, Italy

[21] Appl. No.: 406,298

[22] Filed: Sep. 12, 1989

[30] Foreign Application Priority Data

Sep. 16, 1988 [IT] Italy .................. 21965 A/88

[51] Int. Cl.[5] .......... A61K 9/20; A61K 9/08; A61K 9/14; A61K 31/489
[52] U.S. Cl. .................. 424/440; 424/441; 424/458; 514/850
[58] Field of Search .......... 424/440, 441, 458; 514/289, 850

[56] References Cited

U.S. PATENT DOCUMENTS

| | | | |
|---|---|---|---|
| 2,744,112 | 5/1956 | Vogler | 546/149 |
| 4,126,684 | 11/1978 | Robson et al. | 514/271 |
| 4,788,055 | 11/1988 | Fischer et al. | 514/850 |
| 4,806,543 | 2/1989 | Choi | 514/464 |
| 4,906,638 | 3/1990 | Pontecorso et al. | 514/282 |

*Primary Examiner*—Thurman Page
*Assistant Examiner*—E. J. Webman
*Attorney, Agent, or Firm*—Walter H. Schneider

[57] ABSTRACT

Dextrorphan salts with polycarboxylic organic acids are effectively absorbed by the oral route and can conveniently be formulated in pharmaceutical compositions suitable to the oral administration.

3 Claims, No Drawings

ORAL PHARMACEUTICAL COMPOSITIONS CONTAINING DEXTROPHAN SALTS

The present invention relates to oral pharmaceutical compositions containing dextrorphan salts as the active ingredient.

Dextrorphan is known to be the main metabolite of dextromethorphan, which is a drug widely used as an antitussive agent. The activity of dextromethorphan is due for the major part to the one of dextrorphan which displays a remarkable antitussive action as well as other desirable characteristics, such as lack of analgesic activity and of affinity to the opiaceous receptors. Moreover, dextrorphan has a very low toxicity, even lower than that of dextromethorphan. As a consequence, the therapeutical use of dextrorphan in substitution of or alternatively to dextromethorphan has already been proposed. Thus, for example, EP-A-86201665.7 discloses pharmaceutical compositions containing dextrorphan for intranasal administration.

Even though dextrorphan has previously been reported not to be conveniently used by the oral route (Schanker L. S., Shore Parkhurst P. A., Brodie B. B., Hoghen C. A. M., J. Pharmacol. Exp. Therap. 120, 528, 1957), it has been found, and it is the object of the invention, that dextrorphan salts with organic acids are efficiently absorbed by the oral route, attaining pharmacologically significant hematic levels of dextrorphan.

According to the invention, therefore, oral pharmaceutical compositions are provided containing, as the active ingredient, dextrorphan organic acid salts.

Particularly preferred are the polycarboxylic organic acids, specifically di- or tri-carboxylic acids. The use of citric and tartaric acids as the salifying agents is most preferred.

The compositions according to the invention contain 1 to 100 mg of dextrorphan salts per unitary dose, more preferably 5 to 50 mg. Suited administration forms are tablets, controlled - release tablets, sublingual tablets, chewable tablets, sugar-drops, granulate sachets for extemporary dissolution, drops, syrups and the like. Said compositions are prepared according to conventional techniques and excipients, such as those described in "Remington's Pharmaceutical Sciences Handbook", Hack Pub. Co., N.Y., U.S.A..

The compositions of the invention can be administered one or more times daily, according to the severity of the disease to be treated and to the conditions of the patient.

The results from a pharmacokinetic study effected on guinea pigs under urethane anesthaesia, to which dextrorphan citrate and tartrate had been administered by the oral route, are reported hereinbelow in order to show the good bioavailability of dextrorphan salts.

Dextrorphan dosages were measured by a high pressure liquid chromatography method.

The plasma samples were subjected, before the extraction, to enzymatic hydrolysis with $\beta$-glucuronidase, according to the method reported by T.EAST and D.DYE (Journal of Chromatography Biomedical Applications 388, 99-112, 1985).

After hydrolysis, plasma samples were alkalinized with sodium carbonate and extracted with benzene; benzene was re-extracted with 0.5 ml of 0.1 NHCl and 100 mcl were chromatographed under the following conditions:

COLUMN: Lichrosorb RP Select B Merck 5 $\lambda$, 25 cm $\times$4 mm inn. d.

MOBILE PHASE: Octanesulphonic acid sodium salt 0.01M solution in water. Acetonitrile mixture (68-32% ). The solution was then buffered to pH 3 with phosphoric acid.

FLOW: 0.8 ml/minute

DETECTOR: F 1000 MERCK HITACHI Fluorimeter exc.=280 nm ; em.=310 nm

Dextrorphan citrate and tartrate turned out to be effectively absorbed, as evidenced in Tables 1 and 2 which follow.

TABLE 1

| Time (minutes) | Dextrorphan hematic levels mcg/ml |
| --- | --- |
| 15 | 0.07 |
| 30 | 0.3 |
| 60 | 0.95 |
| 120 | 4.1 |
| 180 | 4.2 |
| 300 | 5 |

TABLE 2

| Time (minutes) | Dextrorphan hematic levels mcg/ml |
| --- | --- |
| 15 | 0.01 |
| 30 | 0.47 |
| 60 | 2.5 |
| 120 | 3.8 |
| 180 | 3.0 |
| 300 | 3.8 |

The following non limitative examples further illustrate the pharmaceutical compositions according to the invention.

EXAMPLE 1

| SYRUP | |
| --- | --- |
| 100 ml of syrup contain: | |
| Dextrorphan citrate | 0.1-1 g |
| Benzoic acid | 0.090 g |
| Sodium benzoate | 0.050 g |
| Flavors | 0.160 g |
| Saccharose | 72 g |
| Depurated water | q.s. to 100 ml |

EXAMPLE 2

| DROPS FOR ORAL USE | |
| --- | --- |
| 100 ml of solution contain: | |
| Dextrorphan citrate | 1-5 g |
| Parabens | 0.1 g |
| Flavors | 1,5 g |
| Depurated water | q.s. to 100 ml |

EXAMPLE 3

| TABLETS | |
| --- | --- |
| One of tablet contains: | |
| Dextrorphan citrate | 5-50 mg |
| Maize starch | 90 mg |
| Lactose | 20 mg |
| Talc | 10 mg |
| Magnesium stearate | 0.2 mg |

EXAMPLE 4

CONTROLLED - RELEASE TABLETS
One tablet contains:

| | |
|---|---|
| Dextrorphan citrate | 5-50 mg |
| Hydroxypropylmethylcellulose | 117 mg |
| Anhydrous lactose | 80 mg |
| Magnesium stearate | 5 mg |
| Precipitated silica | 3 mg |

EXAMPLE 5

SUBLINGUAL TABLETS
One sublingual tablet contains:

| | |
|---|---|
| Dextrorphan citrate | 5-50 mg |
| Flavors | 10 mg |
| Talc | 10 mg |
| Polyvinylpyrrolidone | 4 mg |
| Magnesium stearate | 0.2 mg |
| Lactose<br>Saccharose | q.s. to 150 mg |

EXAMPLE 6

CHEWABLE TABLETS
One tablet contains:

| | |
|---|---|
| Dextrorphan citrate | 5-50 mg |
| Aspartame | 30 mg |
| Flavors | 10 mg |
| Magnesium stearate | 10 mg |
| Sorbitol<br>Mannitol | q.s. to 1 g |

CHEWABLE TABLETS
One tablet contains:

| | |
|---|---|
| Lactose | |

EXAMPLE 7

SUGAR-DROPS
One sugar-drop contains:

| | |
|---|---|
| Dextrorphan citrate | 5-50 mg |
| Flavors | 20 mg |
| Glucose | 1 mg |
| Saccharose | 1,5 g |

EXAMPLE 8

SACHET FOR EXTEMPORARY DISSOLUTION
5 g of granulate contain:

| | |
|---|---|
| Dextrorphan citrate | 5-50 mg |
| Aspartame | 60 mg |
| Flavors | 20 mg |
| Sorbitol<br>Mannitol<br>Lactose | q.s. to 1 g |

We claim:

1. A method of treating a tussive condition which comprises the oral administration to a patient of an effective amount for treating a tussive condition of a composition the principal active ingredient of which is dextrorphan citrate in admixture with a pharmaceutical acceptable carrier.

2. A method according to claim 1 in which the composition is orally administered as a unit dosage comprising the principal active ingredient in an amount of 1.0-100 mg.

3. A method according to claim 2 in which the unit dosage is in the form of a tablet, sachet, syrup or drop.

* * * * *

UNITED STATES PATENT AND TRADEMARK OFFICE
CERTIFICATE OF CORRECTION

PATENT NO. : 5,013,554

DATED : May 7, 1991

INVENTOR(S) : Carlo Passarotti; Antonio Fossati; Mauro Valenti; Gianluigi Bandi

It is certified that error appears in the above-identified patent and that said Letters Patent is hereby corrected as shown below:

Title page, item [75], "Carlos" should read --Carlo--.

Signed and Sealed this

Twenty-second Day of September, 1992

Attest:

DOUGLAS B. COMER

*Attesting Officer*    *Acting Commissioner of Patents and Trademarks*

UNITED STATES PATENT AND TRADEMARK OFFICE
CERTIFICATE OF CORRECTION

PATENT NO. : 5,013,554

DATED : May 7, 1991

INVENTOR(S) : Carlo Passarotti; Antonio Fossati; Mauro Valenti; Gianluigi Bandi

It is certified that error appears in the above-identified patent and that said Letters Patent is hereby corrected as shown below:

Title page, item [75], "Carlos" should read --Carlo--.

Signed and Sealed this

Twenty-ninth Day of September, 1992

Attest:

DOUGLAS B. COMER

*Attesting Officer*  *Acting Commissioner of Patents and Trademarks*